United States Patent
Hoenes et al.

(10) Patent No.: US 9,480,427 B2
(45) Date of Patent: Nov. 1, 2016

(54) LANCET

(75) Inventors: Joachim Hoenes, Zwingenberg (DE); Hans List, Hesseneck-Kailbach (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 329 days.

(21) Appl. No.: 13/453,445

(22) Filed: Apr. 23, 2012

(65) Prior Publication Data

US 2013/0116718 A1    May 9, 2013

(30) Foreign Application Priority Data

May 6, 2011 (EP) .................................... 11003732

(51) Int. Cl.
| | |
|---|---|
| *A61B 5/00* | (2006.01) |
| *A61B 5/151* | (2006.01) |
| *A61B 5/15* | (2006.01) |

(52) U.S. Cl.
CPC ............ *A61B 5/151* (2013.01); *A61B 5/1411* (2013.01); *A61B 5/150022* (2013.01); *A61B 5/150282* (2013.01); *A61B 5/150358* (2013.01); *A61B 5/150419* (2013.01); *A61B 5/150511* (2013.01)

(58) Field of Classification Search
CPC .......... A61B 5/1411; A61B 17/32093; A61B 5/151; A61B 5/150022; A61B 5/150419; A61B 5/150358; A61B 5/150282
USPC .................................. 606/181; 600/585, 584
See application file for complete search history.

(56) References Cited

U.S. PATENT DOCUMENTS

| | | | |
|---|---|---|---|
| 2,896,628 A * | 7/1959 | Speelman ..................... | 606/181 |
| 3,046,987 A | 7/1962 | Ehrlich | |
| 7,993,284 B2 | 8/2011 | Effenhauser et al. | |
| 8,052,618 B2 | 11/2011 | Haar et al. | |
| 2003/0028125 A1 | 2/2003 | Yuzhakov et al. | |
| 2003/0212344 A1 | 11/2003 | Yuzhakov et al. | |
| 2004/0096959 A1 | 5/2004 | Stiene et al. | |
| 2005/0171567 A1* | 8/2005 | DeHart ........................ | 606/181 |
| 2006/0008389 A1 | 1/2006 | Sacherer et al. | |
| 2007/0038149 A1* | 2/2007 | Calasso et al. ............... | 600/583 |
| 2007/0197937 A1* | 8/2007 | Sarofim et al. ............... | 600/583 |
| 2008/0009768 A1* | 1/2008 | Sohrab .......................... | 600/583 |
| 2009/0099477 A1 | 4/2009 | Hoenes et al. | |
| 2009/0240165 A1* | 9/2009 | Yoneya et al. ................ | 600/583 |

(Continued)

FOREIGN PATENT DOCUMENTS

| | | |
|---|---|---|
| EP | 1 360 932 A1 | 11/2003 |
| EP | 1 911 394 A1 | 4/2008 |

(Continued)

*Primary Examiner* — Richard Louis
(74) *Attorney, Agent, or Firm* — Woodard Emhardt Moriarty McNett and Henry LLP

(57) ABSTRACT

The invention relates to a lancet, which has a lancet tip at a front end and which on an upper face comprises a contact surface for placing a test element thereon and at least one channel for receiving a sample, wherein an upwardly open section of the channel runs in the contact surface. According to the invention, the channel has another upwardly open channel section which runs on the upper face of the lancet in or adjacent to a surface area that is lower than the contact surface, wherein the contact surface is arranged between the lancet tip and the lower surface area. The invention further relates to a system comprising such a lancet and a test element, and to a method for transferring a liquid sample from a channel of a lancet which is designed as a groove or slot to a test element.

14 Claims, 1 Drawing Sheet

(56) References Cited

U.S. PATENT DOCUMENTS

| | | | |
|---|---|---|---|
| 2009/0247841 A1* | 10/2009 | Werner | A61B 5/1411 600/310 |
| 2010/0010375 A1 | 1/2010 | Haar et al. | |
| 2010/0049091 A1 | 2/2010 | Haar | |
| 2010/0331730 A1 | 12/2010 | Naito et al. | |
| 2011/0230905 A1 | 9/2011 | Roe et al. | |
| 2012/0041340 A1 | 2/2012 | Konya | |
| 2012/0071791 A1 | 3/2012 | Hoenes | |

FOREIGN PATENT DOCUMENTS

| | | |
|---|---|---|
| EP | 2 263 526 A1 | 12/2010 |
| WO | WO 2004/064636 A1 | 8/2004 |
| WO | WO 2005/084530 A2 | 9/2005 |
| WO | WO 2008/122541 A1 | 10/2008 |
| WO | WO 2010/142728 A1 | 12/2010 |

* cited by examiner

LANCET

CROSS-REFERENCE TO RELATED APPLICATION

This application claims the benefit of European Patent Application No. 11 003 732.2, filed May 6, 2011, the entire disclosure of which is hereby incorporated by reference.

BACKGROUND

The invention relates to a lancet which on an upper face comprises at least one upwardly open channel for receiving a sample.

Upon lancing the body of a patient, the channel fills with body fluid, generally blood or interstitial liquid, due to capillary forces. Lancets comprising such capillary channels thus allow easy withdrawal of small samples of body fluids and thereby facilitate measurements of the concentrations of medically significant analytes, for example glucose or lactate.

So as to measure the analyte concentration, the sample must be transferred to a test field which contains detection reagents. Such a test zone can be provided directly on the lancet, as is known from WO 2005/084530 A2. The sample is then transported in the channel to the test zone by way of capillary forces.

An alternative to lancets comprising integrated test fields are systems which include lancets and separate test elements. In such systems, a sample is transferred from the channel to the test element by pressing the lancet against the test element, which is to say the upper face of the lancet forms a contact surface for placing a test element thereon. The sample contained in the channel can then be taken up by the test element. Such a system is known from EP 2263526 A1, for example. Test elements and lancets can be arranged on a carrier tape or they can be present as loose, individual parts of the system.

Providing test fields on lancets is complex for manufacturing reasons. Systems composed of lancets and separate test elements thus have the advantage of being comparatively inexpensive to manufacture, however the transfer of sample fluid from a lancet to a test element is problematic.

SUMMARY

It is an object of the present invention to show a way of how a liquid sample can be better transferred from a channel of a lancet to a separate test element.

This object is achieved by a lancet which has a lancet tip at a front end and which on an upper face comprises a contact surface for placing a test element thereon and at least one channel for receiving the sample. An upwardly open section of the channel runs in the contact surface. According to the invention, the channel has another upwardly open channel section, which runs in the upper face of the lancet adjoining a surface area that is lower than the contact surface or which runs in the upper face of the lancet in a surface area that is lower than the contact surface. The contact surface is arranged between the lancet tip and the lower surface area.

If the upper face of a lancet according to the invention is covered by a test element, a capillary gap forms between the lower surface area and the test element. Sample liquid can then be transported by way of capillary forces from the channel into the capillary gap between the lower surface region of the lancet and the test element. The surface of the test element which is located opposite the lower surface area of the lancet can thus be wetted over a large surface area.

Whereas coverage of the channel of a conventional lancet, which runs horizontally in a plane, results in wetting of the test element only along a narrow line along which the channel is in contact with the test element, a lancet according to the invention allows improved transfer of the sample to be combined with a spreading effect, whereby a larger surface area on the test element is wetted. A capillary gap between the lower surface area and a test element which is placed on the contact surface for the sample transfer fills both in the direction of the channel and transversely thereto due to capillary forces. This is a significant advantage, especially for a photometric evaluation of a detection reaction of the test field. Because of the spreading action during a sample transfer to a test field, the lower surface area of the lancet is also referred to as a spreading area.

When the section of the capillary channel runs in the spreading surface, the capillary gap forms on both sides of the channel. For a spreading transfer of the sample, however, it is generally sufficient if the capillary gap forms only on one side of the channel. In this case, the contact surface can extend on one side laterally along the channel, while the lower surface area is present on the other side of a channel section, whereby a capillary gap is formed only on this other side when a test element is placed on the contact surface of the lancet.

Because the channel of a lancet according to the invention leads into a lower surface region, the channel extends not only in a single geometrical plane. In addition to a transport of the liquid in a longitudinal direction of the channel also a transport in a direction which has a component perpendicular to the upper face of the lancet, which is to say downward, is effected. When the channel is covered by a test element, the upper face of the test element can come in contact with a starting section of the channel, which is to say an upper channel section extending in front of the depression, and liquid contained therein can wet this section.

In a lancet according to the invention, the term "front" shall be understood to mean the end comprising the lancet tip. The term "behind" accordingly denotes the end facing away from the lancet tip. The information "front" and "behind" thus refers to the lancing direction, which is to say along the longitudinal direction of the lancet away from the lancet tip. In a lancet according to the invention, the upper face denotes the side of the lancet which comprises the channel for receiving the sample and the contact surface on which a test element is placed for transferring the sample. Accordingly, "top" denotes the direction perpendicular to the lancing direction and perpendicular to the width of the lancet. The "top" direction in general is the direction perpendicular to the contact surface. The expression "lower" thus denotes a position which toward the top has a distance from a geometric plane in which the contact surface is located. Geometric planes which are parallel to the contact surface and are located below the contact surface are thus "lower".

The capillary channel can lead downward into the lower surface area with an inclined channel section. However, it is also possible for the channel to have a bottom which is located at a constant height, which is to say the channel depth is higher in the contact surface than in the lower surface area. Thereby the difference in height can be compensated for.

The lower surface area may form a base of an upwardly open depression into which the channel leads, e.g. with an inclined channel section. By providing the upper face of the lancet with a depression, the upper face of the lancet can form two contact surfaces for placing a test element, for example a test strip, thereon. The depression is then located between the two contact surfaces, as seen looking in the longitudinal direction of the lancet. If the upper face of the lancet is covered by a test element, the element thus rests against two contact surfaces between which the lower surface area is present. The capillary gap forming between the test element and lancet is then well defined, in particular when the two contact surfaces are located at the same height.

However, a well defined capillary gap between the lancet and test element can also be achieved with a lancet which instead of a depression between the two contact surfaces comprises, on the upper face, only a single step, whereby the contact surface above the lower surface area provides only a single surface area. In such a case, a test element which comprises a complementary step, e.g. a spacer, can be used instead of a flat test element. The spacer can, for example, be a piece of film that is glued onto a part of the surface of a test strip, whereby a step is formed. For receiving a sample, the spacer of the test element is then placed on the lower surface area of the lancet while another section of the test element is placed on the contact surface of the lancet. In principle, such a spacer can also be integrated in a measuring device which places a test element on a lancet and then measures an analyte content in a sample thereby transferred to the test element, for example the glucose content.

In a system comprising a lancet according to the invention and a test element, a spacer can thus be provided which predetermines a distance between a surface area on the upper face of the lancet and a sample receiving surface area of the test element so as to form the capillary gap.

A lancet according to the invention may comprise a depression on the upper face, an inclined section of the channel leading downward into the depression and another inclined section of the channel leading upward out of the depression. The channel runs in the depression between the two inclined sections, for example in that the channel is cut into the depression, for example by means of etching or laser cutting. During lancing of the body of a patient, the channel fills with body fluid due to capillary forces. The lancet according to the invention in this case thus has a capillary channel which traverses the upwardly open depression, wherein a section of the channel is arranged in a base of the depression.

An inclined channel section which leads downward into the depression, or upward out of the depression, can be slanted, which is to say it can have a substantially constant slope, or it can be curved, which is to say it can have a slope that changes along the inclined section.

If the channel traverses the depression, it can be achieved that a capillary gap between a test element, which covers the upper face of the lancet for transferring a sample, and the surface of the lancet in the depression fills quickly. The channel is preferably cut into the upper face of the lancet and into the depression, for example by means of etching or laser cutting.

The channel can be designed as a groove or as a slot. A first section of such a groove or slot can run between the tip and the depression, which is to say in the contact surface. A second section of the groove or slot runs in a surface area which is lower than the contact surface, or along such a surface area.

The contact surface and the lower surface area are preferably flat. A horizontal section of the channel then runs in the lower surface area. It is also possible for a channel section leading out of the depression to directly adjoin a section leading into the depression. The section in the depression can have a flat design, which is to say run parallel to a channel section that is provided in the contact surface.

By arranging a channel section in front of the depression and another channel section behind the depression, the channel can receive a larger amount of liquid, which is then available to fill a capillary gap between the upper face of the lancet in the region of the depression and the test element.

According to a further advantageous refinement of the invention, the lancet comprises a shaft which ends in the lancet tip, wherein at least a part of the lower surface area is arranged in the shaft. A shaft shall be understood to mean a narrow region of a lancet which is introduced entirely or partially into the body of a patient during lancing. In the case of many lancets, a wider section adjoins the shaft and allows a lancet to be held, for example, in a holder of a lancing device.

In principle, the spreading surface, which is a lower surface area, can also be arranged in a widened section of the lancet body which adjoins the shaft. By arranging at least a portion of the spreading surface in the shaft, the sample liquid taken up during lancing can be transported more quickly into the channel section which runs in the lower surface area or along it. A channel section in the spreading surface can notably take up sample liquid even while the lancet is still introduced in the body of a patient. During lancing, in such a case the section of the shaft which comprises the spreading surface can be introduced entirely or partially into the body of a patient. However, this is not required. The spreading surface may also start on the shaft such a large distance away from the tip that, during lancing, the spreading surface is normally not introduced in the body of the patient.

According to a further advantageous refinement of the invention, the spreading surface adjoins lateral surfaces of the lancet on one side or on both sides. This means that the spreading surface extends at least up to one lateral surface of the lancet. The lateral surfaces of the lancet then comprise recesses in their edges. In the region of the spreading surface, the lateral edges of the upper face of the lancet are thus likewise depressed. The spreading surface can thus extend across the full width of the lancet, which the lancet has in the region of the spreading surface. When placing a test element thereon, maximum distribution of sample liquid on the test element transversely to the channel direction is thus made possible. A capillary gap between a test element placed on the upper face of the lancet and the lancet is thus not delimited transversely to the channel direction, and instead can extend across the full width of the lancet in the region of the spreading surface. Especially when the spreading surface is arranged entirely or partially in the shaft of the lancet, advantageously large spreading of sample liquid on a test element can thus be achieved.

A lancet according to the invention is preferably designed as a flat lancet, which is to say it is produced from sheet metal or another strip material. The lancet is particularly preferably made of sheet metal, wherein a difference in height exists between the lower surface area and the contact surface. The difference is preferably less than the metal sheet thickness, e.g. less than half the metal sheet thickness.

According to a further advantageous refinement of the invention, a difference in height which is smaller than the maximum depth of the channel exists between the spreading surface, this being the lower surface area, and the contact surface.

In a lancet according to the invention, a difference in height exists between a channel section in the spreading surface and a channel section in the contact surface. This difference in height can be overcome by an inclined channel section leading downward into the depression.

The difference in height here shall be understood to mean the difference between the heights at which the respective upper edges of the respective channel sections, which is to say the lateral delimitations thereof, are located in the spreading surface and in the contact surface. The depth of a channel should be measured from the base of the groove to the upper edge thereof for a channel that is designed as a groove. For a channel designed as a slot that goes all the way through the lancet body, i.e. is open on the top and the bottom surface of the lancet, the depth is predetermined by the material thickness of the lancet body in which the slot is located.

The difference in height is preferably less than the maximum depth of the channel. If the lancet is cut from sheet metal, the difference in height is preferably less than the metal sheet thickness, and more particularly less than half the thickness of the metal sheet. The height difference is preferably at least 10 µm, particularly preferably at least 20 µm, and more particularly at least 30 µm. The difference in height is preferably less than 150 µm, particularly preferably less than 100 µm, and more particularly less than 80 µm. In the spreading surface, the width of the channel is preferably between half and twice the difference in height. The width of the channel in the depression is particularly preferably greater than the difference in height.

The lancet, in principle, can comprise several channels, which can be arranged next to one another, for example, so as to increase the amount of body liquid received during lancing. However, a single channel is sufficient.

The spreading surface can be designed between two bending zones in which the lancet is bent. A respective inclined section of the channel then runs in each of these two bending zones. The depression can be implemented, for example, by means of deep drawing or embossing. The channel can be etched, for example.

A lancet according to the invention and a test element, which can be used to cover the channel of the lancet after a lancet puncture, together form a system. The lancet is may be surrounded by a sterile protector and the test element mounted outside the sterile protector of the lancet.

The invention also relates to a method for transferring a liquid sample from a channel of a lancet, which may designed as a groove or a through slot, to a test element by covering the channel with the test element, wherein the test element is placed on a first surface region of the lancet in which a first section of the channel runs. Thereby a capillary gap is formed between a second surface region of the lancet in which a second section of the channel runs and the test element so that liquid from the channel penetrates into the capillary gap due to capillary forces. The first surface region of the lancet thus forms a contact surface and the second surface region forms a spreading surface.

The upper face of a lancet according to the invention preferably forms two contact surfaces to place a test element on for such a method. As seen looking in the longitudinal direction of the lancet, the spreading surface is then located between the two contact surfaces, which are preferably flat and located at the same height.

BRIEF DESCRIPTION OF THE DRAWINGS

Further details and advantages of the invention will be described based on an exemplary embodiment with reference to the accompanying drawings. In the drawings.

DETAILED DESCRIPTION

Figure 1:
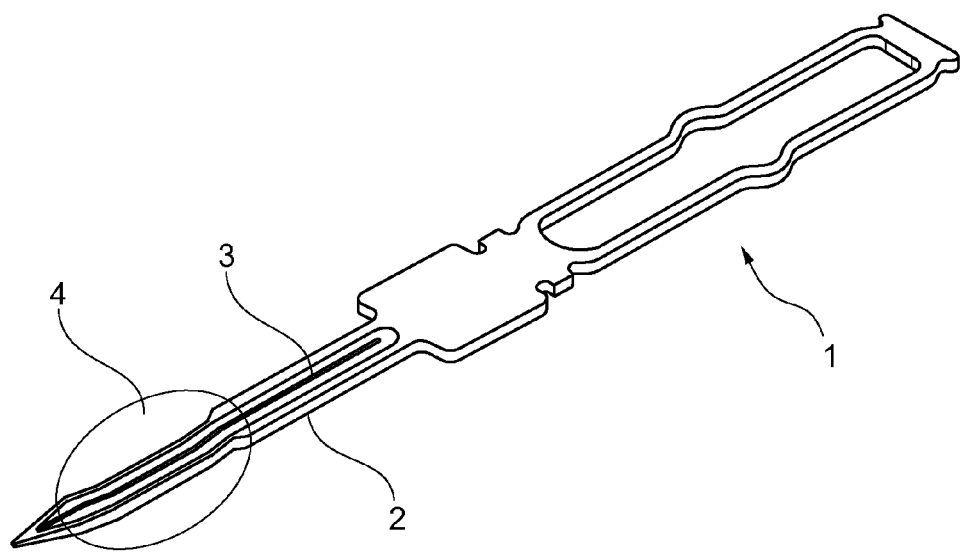
FIG. 1 is an exemplary embodiment of a lancet.

The lancet 1 shown in FIG. 1 with a view onto the upper face thereof comprises a lancet body having a shaft 2, which ends in a tip. On the upper face, the lancet 1 has an upwardly open channel 3 for receiving a sample. In the exemplary embodiment shown, the channel 3 is designed as a groove. It can also be a slot, for example, which extends from the upper face to the lower face of the lancet 1. When the lancet 1 is introduced in the body of a patient, the channel 3 fills with body fluid due to capillary forces. The channel 3 is thus a capillary channel.

In the circled region 4, the upper face of the lancet 1 comprises an upwardly open depression, which is to say the depression is not covered. An inclined section of the channel 3 leads downward into the depression. The channel 3 thus has a sloping section which overcomes a difference in height between the base of the depression and the upper face of the lancet 1 next to the depression.

Figure 2:
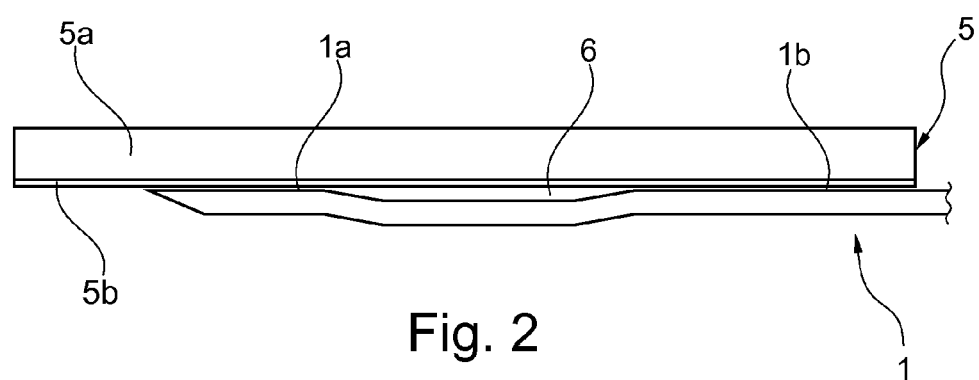
FIG. 2 is a schematic illustration of a front section of the lancet comprising a test element placed on the lancet for transfer of the sample.

So as to transfer a body fluid sample from the channel 3 to a test element 5, the upper face of the lancet 1 is placed on a test element 5 as shown schematically in FIG. 2. The upper face of the lancet 1 thus has contact surfaces for placing a test element 5 thereon, wherein the depression is located between the two contact surfaces 1a, 1b schematically indicated in FIG. 2. When a test element 5 is placed on the lancet 1, a capillary gap 6 forms between the test element 5 and the lancet 1 in the region of the depression. The capillary gap 6 fills with sample liquid from the channel 3 and thus effects a spreading action during the transfer of the sample. The base of the depression is thus referred to as a spreading surface.

The channel 3 begins with a starting section in the front contact surface 1a, which is arranged between the tip and the depression. The channel 3 extends through the depression, as shown in FIG. 1. A section of the channel 3 is thus arranged in the base of the depression. As seen looking from the lancet tip, the channel initially leads downward into the depression and then upward again out of the depression. In other words, the channel 3 has two inclined sections. In an inclined channel section, the channel edges also have a sloping progression.

A section of the channel 3 leading downward into the depression and a section thereof leading upward out of the depression are preferably connected to each other by a flat channel section. The flat channel section can be shorter than the channel section leading downward into the depression, but preferably it is longer, for example twice as long or longer.

In the exemplary embodiment shown, the depression is arranged between two flat sections of the channel 3. A first flat section of the channel 3 is arranged in front of the depression, as seen looking from the tip of the lancet 1. A second flat section of the channel 3 is arranged behind the depression, as seen looking from the tip. In the exemplary embodiment shown, the channel 3 does not start until a short distance from the tip, which is to say at a distance from the front end of the lancet 1 in the lancing direction. However, the channel 3 can also continue to the tip, which is to say it can be open in the lancing direction.

When the upper face of the lancet 1 is placed on a test element 5, the test element 5 is wetted by the two channel sections between which the depression is located. The capillary gap 6 formed between the lancet 1 in the region of the depression and the test element 5 is then filled from both ends.

The channel 3 can be cut into the surface of the lancet 1, and more particularly into the depression, for example by means of etching. As shown in FIG. 2, the depression can extend into the lateral surfaces of the lancet 1. The depression then extends across the entire width of the lancet 1 at this point.

The preferred material for the lancet 1 is sheet metal. In principle, however, the lancet can also be produced from other materials, for example plastic or ceramic material. Flat lancets are cost-effective to produce by cutting a lancet body from a strip material, for example sheet metal, such as by means of etching, stamping or laser cutting.

The depth of the depression defines the width of the capillary gap 6 between the test element 5 and lancet 1 shown in FIG. 2. Good capillary action can already be achieved at a difference in height of 10 µm between the regions of the lancet 1 placed on the test element 5 and the depression. The depression can have a depth between 10 µm and 200 µm, for example. The depth of the depression preferably agrees with the difference in height between a channel section in the depression and a channel section outside the depression.

The depth of the depression is preferably less than the material thickness of the lancet body, which is to say, for example, less than the thickness of the sheet metal from which the lancet body can be cut. The depth of the depression can, for example, be less than half the material thickness.

Because even a small depression is sufficient, the depth of the depression can be less than the maximum depth of the channel 3. The depth of the channel 3 can be substantially constant in the depression, and more particularly it can agree with the channel depth of a channel section outside the depression. In the exemplary embodiment shown, the depth of the depression ranges between 10% and 80% of the depth of the channel 3 in the depression. However, a lancet according to the invention can also be produced in deviating dimensions of the depression than those mentioned here within the scope of the description of the figures.

In the exemplary embodiment shown, the width of the channel 3 in the depression ranges between half and twice the difference in height, for example the width of the channel 3 in the depression is greater than the difference in height. Such dimensions are not absolutely necessary. The width of the channel 3 in the depression can be substantially constant, as shown in FIG. 1.

The width of the channel 3 can be substantially constant in the depression. In particular, the width of the channel 3 in the depression can be the same as in sections in front of and behind the depression. The channel 3 can have a substantially rectilinear progression over the entire length, as shown in FIG. 1. Such a channel 3 can be arranged particularly well on a narrow lancet shaft 2. However, it is also possible for the channel 3 to have curves.

In the exemplary embodiment shown, the depression is arranged entirely in the lancet shaft 2. In principle, however, the depression can also be arranged in a wider section of the lancet body which adjoins the shaft 2. By arranging the depression at least partially in the shaft 2, it can be achieved that the channel 3 in the region of the depression fills more quickly during lancing and a sample can thus be transferred more quickly and more reliably to the test element 5 placed on the surface of the lancet 1.

The test element 5 shown schematically in FIG. 2, together with the lancet 1, forms a system. The test element 5 comprises a carrier 5a having a layer of detection reagents 5b, which effect a detection reaction in the presence of a liquid sample, for example for photometric concentration determination. The lancet 1 and the test element 5 are designed such that, when the channel 3 of the lancet 1 is covered by the test element 5, a capillary gap 6 forms between the test element 5 and the lancet 1 in the region of the depression, the capillary gap taking up liquid from the channel 3. In the exemplary embodiment shown, the test element 3 has a flat surface, which is to be placed on flat surface sections of the lancet 1 between which the depression is located. In principle, however, it is also possible for the test element 5 to be designed with a curved surface and for the upper face of the lancet 1 to be designed in a corresponding shape.

The test element 5 and the lancet 1 can be packaged in different magazines or stored in one common magazine. In any case, a test element is placed on the contact surface 1a, 1b of the lancet 1 not until after lancing. Until lancing, the lancet is surrounded by a sterile protector, which can, for example, be designed as a magazine chamber or as a protective film, which together with a carrier tape surrounds a volume containing the lancet. Several lancets can be arranged on such a carrier tape. Test elements can be arranged between the lancets on the carrier tape.

REFERENCE NUMERALS

1 Lancet
1a, b Contact surface
2 Shaft
3 Channel
4 Region
5 Test element
6 Capillary gap

The invention claimed is:

1. A lancet comprising
a lancet tip at a front end, and
an upper face with a contact surface for placing a test element thereon, said upper face comprising at least one channel configured to draw a sample via capillary action, an upwardly open section of the channel running in the contact surface, wherein the channel has a bottom,
characterized in that
the channel has another upwardly open channel section, which runs on the upper face of the lancet in a lower surface area of the upper face of the lancet, the lower surface area being lower in height than the contact surface and the lancet tip, wherein the contact surface is arranged between the lancet tip and the lower surface area, and
the two channel sections are connected by an inclined channel section which leads downward into the lower surface area, wherein the bottom of the channel at the inclined channel section is inclined.

2. A lancet according to claim 1, characterized in that the lancet comprises a shaft, wherein the lower surface area is arranged at least partially in the shaft.

3. A lancet according to claim 1, characterized in that the lancet is made of sheet metal, wherein a difference in height exists between the lower surface area and the contact surface, the difference being less than the metal sheet thickness, and more preferably less than half the metal sheet thickness.

4. A lancet according to claim 1, characterized in that there is a difference in height between the lower surface area and the contact surface, said difference being smaller than the maximum depth of the channel.

5. A lancet according to claim 1, characterized in that the section of the channel in the contact surface is a starting section of the channel.

6. A lancet according to claim 1, characterized in that the lower surface area forms a base of a depression into which the channel leads.

7. The lancet according to claim 6, characterized in that the channel traverses the depression.

8. The lancet according to claim 6, characterized in that the upper face comprises a further contact surface for placing a test element thereon, wherein the depression is located between the two contact surfaces in the longitudinal direction of the lancet, and wherein the contact surfaces are flat and located at the same height.

9. A lancet according to claim 1, characterized in that the lower surface area adjoins lateral surfaces of the lancet.

10. A system comprising a lancet according to claim 1 and a test element, by which the channel of the lancet can be covered after lancing, wherein the test element comprises a carrier having a layer of detection reagents which effect a detection reaction in the presence of a liquid sample, wherein the lancet and the test element are designed such that by covering the channel of the lancet with the test element a capillary gap forms between the test element and the lancet, the capillary gap taking up liquid from the channel.

11. The system according to claim 10, characterized in that the capillary gap forms between the test element and a surface area on the upper face of the lancet which is lower than a contact surface of the lancet and in or along which an upwardly open section of the channel runs.

12. The system according to claim 10, characterized in that the capillary gap forms between the test element and a depression which is provided on the upper face of the lancet and into which the upwardly open channel leads.

13. A system according to claim 10, characterized in that a spacer is provided, which predetermines a distance between a surface area on the upper face of the lancet and a sample receiving surface area of the test element so as to form the capillary gap.

14. The lancet according to claim 1, wherein the channel extends continuously from the lancet tip to the lower surface area.

* * * * *